United States Patent [19]

Jamiolkowski et al.

[11] Patent Number: 4,838,267

[45] Date of Patent: Jun. 13, 1989

[54] GLYCOLIDE/P-DIOXANONE BLOCK COPOLYMERS

[75] Inventors: Dennis D. Jamiolkowski, Long Valley; Shalaby W. Shalaby, Lebanon; Rao S. Bezwada, Whitehouse Station; Hugh D. Newman, Jr., Chester, all of N.J.

[73] Assignee: Ethicon, Inc., Somerville, N.J.

[21] Appl. No.: 155,348

[22] Filed: Feb. 12, 1988

[51] Int. Cl.$^4$ .................... A61L 17/00; C08G 63/08
[52] U.S. Cl. .................... 128/335.5; 128/334 R; 525/411; 525/415; 525/937; 528/354; 528/357
[58] Field of Search ............ 525/471, 411, 415; 528/354; 128/335.5

[56] References Cited

U.S. PATENT DOCUMENTS

| | | | |
|---|---|---|---|
| 3,297,033 | 1/1967 | Schmitt et al. | 128/335.5 |
| 4,052,988 | 10/1977 | Doddi et al. | 128/335.5 |
| 4,137,921 | 2/1979 | Okuzumi et al. | 128/335.5 |
| 4,157,437 | 6/1979 | Okuzumi et al. | 528/354 |
| 4,243,775 | 1/1981 | Rosensaft et al. | 525/415 |
| 4,300,565 | 11/1981 | Rosensaft et al. | 128/335.5 |
| 4,643,191 | 2/1987 | Bezwada et al. | 128/335.5 |
| 4,653,497 | 3/1987 | Bezwada et al. | 128/335.5 |

OTHER PUBLICATIONS

Webster, et al., "Practical Suggestions on Facial Plastic Surgery-How I Do It", Laryngoscope, Aug. 1976, vol. 86 (8), pp. 1280-1284.

*Primary Examiner*—Theodore E. Pertilla
*Attorney, Agent, or Firm*—Charles J. Metz

[57] ABSTRACT

Block copolymers of glycolide and p-dioxanone are produced by reacting poly(p-dioxanone) that is substantially free of p-dioxanone monomer with glycolide.

10 Claims, No Drawings

//  4,838,267

GLYCOLIDE/P-DIOXANONE BLOCK COPOLYMERS

The invention relates to block copolymers of glycolide and p-dioxanone.

BACKGROUND OF THE INVENTION

Surgical devices made from glycolide and from p-dioxanone are available commercially in the form of sutures, ligatures, hemostatic clips, surgical staples, and the like. One significant feature of such devices is that they are absorbable in the body, and therefore they eventually disappear from the body after their task has been completed. Representative polymers made from p-dioxanone are described in Doddi et al., U.S. Pat. No. 4,052,988 and representative polymers made from glycolide are described in Schmitt et al., U.S. Pat. No. 3,297,033.

In order to meet specific needs, many different types of polymers containing glycolide and/or p-dioxanone have been proposed. This invention provides block copolymers of glycolide and p-dioxanone that exhibit a high order of initial strength and compliance, but which lose their strength rapidly after implantation in the body. The devices made from the copolymers of the invention, especially sutures, are particularly useful in certain surgical procedures, such as plastic surgery or repair of facial wounds, wherein it is desirable for the device to lose its strength rapidly. One such procedure is known as the "Webster Procedure". It is described in Webster et al., Laryngoscope, Aug. 1976, Vol. 86(8), pages 1280-4, and is a procedure used in plastic surgery or to repair skin lacerations in which a rapidly absorbing suture is used in combination with antitension skin taping. The conventional suturing procedure involved suturing subcutaneous or intradermal tissue with either an absorbable or non-absorbable suture that had to be meticulously removed after two to five days, often with accompanying pain and apprehension. The Webster procedure employs a rapidly absorbing suture so that the implanted portion of the suture will rapidly lose strength, and when the tape is removed a few days later, the external portion of the suture (which, because it was not implanted, did not lose strength) adheres to the tape and is pulled away from the incision. The portion of the suture that was internal, because it loses strength rapidly, breaks and is pulled out with the tape. The pain and discomfort to the patient is much less than when the suture remains intact. Scarring is as good as that resulting from the more usual methods.

BRIEF SUMMARY OF THE INVENTION

The invention provides block copolymers of glycolide and p-dioxanone which have at least about 40 weight percent polymerized glycolide and preferably a major proportion of glycolide. After treatment (such as annealing) to develop crystallinity, the block copolymers of the invention exhibit a glycolide-based crystallinity of at least about 15%, a melting temperature of from about 140° to about 230° C. (the copolymers of the invention may also exhibit a first order transition much lower than the range set forth above), and in the form of surgical filaments, have an initial straight tensile strength of at least about 30,000 psi, and after implantation in the body, lose most (e.g., from 50 to 100%) of their strength in about fourteen days. Annealed filaments made from the copolymers of the invention have substantially higher compliance than do annealed filaments made from polyglycolide homopolymers.

THE PRIOR ART

Rosensaft et al., in U.S. Pat. Nos. 4,243,775 and 4,300,565, and Okuzumi et al., in U.S. Pat. Nos. 4,137,921 and 4,157,437, disclose the preparation of glycolide copolymers by the sequential addition of monomers in a multi-stage Polymerization reaction. Rosensaft et al. disclose that one of the monomers that can be copolymerized with glycolide is p-dioxanone (referred to by the patentees as "2-keto-1,4-dioxane").

DETAILED DESCRIPTION OF THE INVENTION

The copolymers of the invention are prepared by reacting p-dioxanone homopolymer that is essentially free of unreacted monomer (that is, the homopolymer, prior to the copolymerization reaction, contains not more than about 3 or 4 weight percent of unreacted monomer) with glycolide in proportions such that glycolide is present in proportions of greater than about 40 weight percent of the polymerization reaction mixture, preferably greater than about 50 weight percent of the polymerization reaction mixture, more preferably greater than about 60 weight percent of the reaction mixture, and up to about 90 weight percent of the polymerization reaction mixture. The reaction of the p-dioxanone homopolymer with glycolide is preferably carried out in such a manner that the homopolymer is first dissolved (or intimately mixed) in the glycolide monomer before significant polymerization of the glycolide occurs. This is done in order to minimize the presence of homopolymeric species in the final product. It is believed that the copolymers of the invention are block copolymers of the $(A-B)_n$ type.

The crystalline copolymers of the invention are produced by reacting polymerized p-dioxanone substantially free of p-dioxanone monomer (as discussed above), with glycolide monomer. Reacting substantially monomer-free polydioxanone with glycolide (with subsequent polymerization of the glycolide) allows the formation of copolymers that contain polyglycolide blocks or sequences that are capable of developing a significant degree of glycolide-based crystallinity.

As a general rule, the reaction temperature used for the reaction of polydioxanone with glycolide will be within the range of from about 140° C. to about 240° C. When the glycolide content of the reaction mass is less than about 50 weight percent, the reaction temperature is usually within the range of from about 140° C. to about 180° C. When glycolide is the predominant component in the reaction mass, the preferred reaction temperature is usually within the range of from about 200° C. to about 235° C. It is expected that lower reaction temperatures would enhance the formation of blocks by virtue of lowering the incidence of trans-esterification reactions. The examples below illustrate copolymerizations that were carried out in the melt; however, lower temperature solid state polymerizations could also be used.

The copolymers produced in accordance with the invention have melting transitions within the range of from about 140° to about 230° C., glycolide-based crystallinity of at least about 15% and up to, for example, about 40%. The degree of glycolide-based crystallinity may be determined by known procedures such as by X-ray diffraction analysis or by thermal analysis such as Differential Scanning Calorimetry ("DSC"). When X-ray diffraction analysis is employed, the glycolide-based crystallinity is determined by considering only the reflections in the X-ray diffraction pattern which is attributable to the three-dimensional order of polymerized glycolide or polyglycolide units, as opposed to reflections which are attributable to polydioxanone sequences. When the glycolide-based crystallinity is determined by DSC, only the endothermic events attributable to glycolide units are considered. The overall crystallinity of the copolymers of the invention will normally be within the range of from about 25% to about 45%, by X-ray diffraction analysis. (When degree of crystallinity is discussed herein, it is assumed that the material has been treated by methods analogous to those that are known in the art to develop crystallinity. Annealing is the usual procedure used to develop crystallinity.) When the copolymers of the invention are fabricated into dimensionally stable (e.g., annealed to develop at least about 25% total crystallinity) surgical filaments (either monofilaments or braids), they exhibit an initial straight tensile strength of at least about 30,000 psi, and a Youngs modulus of below about 700,000 psi. When the filaments are employed as sutures, they may be attached to surgical needles by conventional procedures. When implanted in the body, these surgical filaments lose most of their strength after about fourteen days (as is evidenced by in vitro studies in pH 7.25 phosphate buffer at 37° C.).

The examples below set forth typical conditions which can be used to prepare the copolymers of the invention. The surgical devices that are made from the copolymers of the invention may be sterilized by conventional procedures, such as by exposure to ethylene oxide by methods that are analogous to those known in the art.

EXAMPLE 1

Typical preparation of p-dioxanone homopolymer

The homopolymer is made by charging pure p-dioxanone, 1-dodecanol (0.192 mol percent), and a catalytic amount of stannous octoate in toluene solution (0.0025 mol percent based on monomer) to an appropriate reactor and heating under an inert dry nitrogen atmosphere at 90° C. for about one hour. Following discharge of the reaction mixture into trays, the reaction mass is heated (by placing the trays in an oven) at 80° C. for 96 hours under dry nitrogen. The polymer is isolated, ground, and dried in vacuo at room temperature for 10 hours and then at 80° C. for 32 hours. (For the first 5 hours of the heated Portion of the drying step, the absolute pressure was 900 microns or below; for the remainder of the step, the absolute pressure was 500 microns or below.) A weight loss of about 4% (predominantly unreacted monomer) is obtained during the vacuum drying. The polymer thus formed has an inherent viscosity ("IV"), determined at a concentration of 0.1 g/dl in hexafluoroisopropyl alcohol at 25° C., of about 1.72 dl/g. (In the examples below, the undyed poly(p-dioxanone) homopolymer used had an IV of 1.72 dl/g.) The polymer contains about 3% residual monomer.

A dyed homopolymer can be made in a similar manner by including about 0.1 weight percent of D and C Violet #2 in the reaction mixture, and by using 0.182 mol percent of 1-dodecanol and 0.004 mol percent stannous octoate catalyst. The resulting dyed homopolymer has an IV of about 1.85 dl/g and contains about 3% residual monomer.

EXAMPLE 2

Preparation of Poly(p-dioxanone-co-glycolide) block copolymer at 20/80 initial weight composition A flame dried, 250 ml, round bottom, single neck flask was charged with 25.0 g of a poly(p-dioxanone) homopolymer prepared as described in Example 1 (this homopolymer will be referred to herein as "PDO"). The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible. (It is believed that after this vacuum heating step, the polymer contained about 2% residual monomer.)

The vessel was removed from the oil bath and allowed to cool. One hundred grams of pure glycolide monomer was introduced into the flask under dry nitrogen. (It is noted that no additional catalyst is introduced; the catalyst remaining in the PDO is usually sufficient to catalyze the copolymerization reaction. As a general rule, the molar Percent of catalyst, based on total mols of p-dioxanone moieties and glycolide in the reaction mass, will be within the range of from about 0.0004 to about 0.004, and preferably from about 0.001 to about 0.002.) The flask was then outfitted with a flame dried mechanical stirrer and an adapter with a hose connection. The flask was purged with dry nitrogen three times before venting with nitrogen. The flask was then placed in a preheated (70° C.) oil bath; the temperature was then reset to 120° C. Twenty-six minutes after the introduction of the reactor into the bath, the bath temperature reached 120° C.; the agitator was partially lowered into the reaction mass at this time and was set to maintain a slow agitation speed. Within 10 minutes at 120° C., the reaction mass was noted to be clear and not very viscous. The stirring speed was then increased. After 15 minutes, the temperature was increased to 140° C. and the stirrer was fully lowered into the reaction mixture. The 140° C. temperature was maintained for 10 minutes; midway through this 10-minute period it was noted that the PDO appeared to be completely dissolved. The temperature was reset to 215° C.; this temperature was achieved in 15 minutes. A bath temperature of 215° C. was maintained for 2 hours. At this stage (and at the corresponding stage in the examples that follow), the vessel was removed from the oil bath and allowed to cool.

The copolymer was isolated, ground, and dried in vacuo at room temperature and at 110° C. for 1.5 and 16 hours, respectively, to remove any unreacted monomer. (The time required to achieve 110° C. is usually about 2 hours after heating is initiated.) A weight loss of 11.1% was observed. The resulting copolymer had a melting range (by hot stage microscopy) of 204°–216° C. with some trace of material melting at 219° C. The copolymer exhibited a single phase melt and recrystallized moderately quickly at temperatures at or just below 195° C. The polymer had an IV of 1.59 dl/g.

EXAMPLE 3

Preparation of Poly(p-dioxanone-co-glycolide) block copolymer at 30/70 initial weight composition A flame dried, 250 ml, round bottom, single neck flask was charged with 37.5 g of PDO. The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible.

The vessel was removed from the oil bath and allowed to cool. Eighty-seven and one-half grams of pure glycolide monomer was introduced into the flask under dry nitrogen. The flask was then outfitted with a flame dried mechanical stirrer and an adapter with a hose connection. The flask was purged with dry nitrogen three times before venting with nitrogen. The flask was then placed in a preheated (70° C.) oil bath; the temperature was then reset to 120° C. Approximately 15 minutes after he introduction of the reactor into the bath, the bath temperature reached 120° C.; the agitator was partially lowered into the reaction mass 10 minutes after reaching 120° C. and was set to maintain a slow agitation speed. After maintaining 120° C. for 20 minutes, the temperature was increased to 140° C. and the stirrer was fully lowered into the reaction mixture and its speed was increased. The 140° C. temperature was achieved in 5 minutes and it was maintained for 5 minutes. The temperature was then reset to 21° C.; this temperature was achieved in 15 minutes, after which the temperature was reset to 215° C. This temperature was achieved in 5 minutes and was maintained for 2 hours.

The copolymer was isolated, ground, and dried in vacuo at room temperature and at 110° C. for 1.5 and 16 hours, respectively, to remove any unreacted monomer. (The time required to achieve 110° C. is usually about 2 hours after heating is initiated.) A weight loss of 23.7% was observed. The resulting copolymer had a melting range (by hot stage microscopy) of 198°–214° C. with some trace of material melting at 218° C. The copolymer exhibited a single phase melt and recrystallized quickly at 180° C. The polymer had an IV of 1.94 dl/g.

EXAMPLE 4

Preparation of Poly(p-dioxanone-co-glycolide) block copolymer at 40/60 initial weight composition A flame dried, 250 ml, round bottom, single neck flask was charged with 50.0 g of PDO. The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible.

The vessel was removed from the oil bath and allowed to cool. Seventy-five grams of pure glycolide monomer was introduced into the flask under dry nitrogen. The flask was then outfitted with a flame dried mechanical stirrer and an adapter with a hose connection. The flask was purged with dry nitrogen three times before venting with nitrogen. The flask was then placed in a preheated (70° C.) oil bath; the temperature was then reset to 120° C. Approximately 20 minutes after the introduction of the reactor into the bath, the bath temperature reached 120° C. After maintaining a temperature of 120° C. for 5 minutes, the agitator was partially lowered into the reaction mass and was set to maintain a slow agitation speed. Five minutes later, the agitation speed was increased. A temperature of 120° C. was maintained for 15 minutes. The temperature was then reset to 140° C. and the stirrer was then fully lowered into the reaction mass. It took 10 minutes to achieve 140° C. The 140° C. temperature was maintained for 5 minutes, and the temperature was then reset to 210° C. After reaching 210° C. (which took 10 minutes), the temperature was reset to 215° C. This temperature was achieved in 5 minutes and was maintained for 2 hours.

The copolymer was isolated, ground, and dried in vacuo at room temperature and at 110° C. for 1.5 and 16 hours, respectively, to remove any unreacted monomer. (The time required to achieve 110° C. was about 2 hours after heating was initiated.) A weight loss of 7.0% was observed. The resulting copolymer had a melting range (by hot stage microscopy) of 190°–210° C. The copolymer exhibited a single phase melt and recrystallized slowly at 180° C. The polymer had an IV of 1.68 dl/g.

The copolymer of Example 4 was analyzed (by proton NMR) and was found to contain 57.1 mol percent polymerized glycolide, 2.1 mol percent glycolide monomer, 40.7 mol percent polymerized p-dioxanone, less than 0.2 mol percent p-dioxanone monomer, and less than 0.1 mol percent 1-dodecanol moiety. The initial 40/60 (by weight) charge of polydioxanone/glycolide is equivalent to a charge of 43.1/56.9 mol/mol ratio.

EXAMPLE 5

Preparation of Polyp-dioxanone-co-glycolide) block copolymer at 50/50 initial weight composition A flame dried, 250 ml, round bottom, single neck flask was charged with 62.5 g of PDO. The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible.

The vessel was removed from the oil bath and allowed to cool. Sixty-two and one-half grams of pure glycolide monomer was introduced into the flask under dry nitrogen. The flask was then outfitted with a flame dried mechanical stirrer and an adapter with a hose connection. The flask was purged with dry nitrogen three times before venting with nitrogen. The flask was then placed in a preheated (70° C.) oil bath; the temperature was then reset to 120° C. Approximately 10 minutes after the introduction of the reactor into the bath, the bath temperature reached 120° C. After maintaining a temperature of 120° C. for 8 minutes, the agitator was partially lowered into the reaction mass and was set to maintain a slow agitation speed. A temperature of 120° C. was maintained for 15 minutes. The temperature was then reset to 140° C., which was achieved in 5 minutes. When the 140° C. temperature was achieved, the stirrer was lowered slightly further. The 140° C. temperature was maintained for 5 minutes, and the temperature was then reset to 210° C. After 5 minutes, the stirrer speed was increased. It required a total of 13 minutes to reach 210° C. After reaching 210° C., the temperature was reset higher and the stirrer was fully lowered into the reaction mass. A temperature of 215° C. was achieved in 2 minutes; the temperature was allowed to increase for 18 more minutes to 225° C. The temperature was lowered to 215° C. in 4 minutes and was maintained there for an additional 1 hour and 38 minutes. The vessel was removed from the oil bath and allowed to cool.

The copolymer was isolated, ground, and dried in vacuo at room temperature and at 110° C. for 1.5 and 16 hours, respectively, to remove any unreacted monomer. (The time required to achieve 110° C. was about 2 hours after heating was initiated.) A weight loss of 4.0% was observed. The resulting copolymer had a melting range (by hot stage microscopy) of 182°–202° C. with some trace of the material melting at 207° C. The copolymer exhibited a single phase melt and recrystallized at temperatures of 180°–160° C. The polymer had an IV of 1.60 dl/g.

The copolymer of Example 5 was analyzed (by proton NMR) and was found to contain 57.4 mol percent polymerized glycolide, 0.4 mol percent glycolide monomer, 42.2 mol percent polymerized p-dioxanone, less than 0.2 mol percent dioxanone monomer, and less than 0.1 mol percent 1-dodecanol-based moiety. The 50/50 (by weight) charge is equivalent to a 53.2/46.8 mol/mol polydioxanone/glycolide charge. The copolymer was also analyzed by carbon-13 NMR to determine the sequence distribution of the copolymer, and it was found that the average chain sequence length ("ACSL") of the polymerized p-dioxanone sequences was 15.8 (plus or minus 3) dioxanone units, and the average ACSL of the polymerized glycolide sequences was 17.0 (plus or minus 3) glycolide units.

EXAMPLE 6

Preparation of Poly(p-dioxanone-co-glycolide) block copolymer at 50/50 initial weight composition A flame dried, 250 ml, round bottom, single neck flask was charged with 62.5 g of PDO. The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible.

The vessel was removed from the oil bath and allowed to cool. Sixty-two and one-half grams of pure glycolide monomer was introduced into the flask under dry nitrogen. The flask was then outfitted with a flame dried mechanical stirrer and an adapter with a hose connection. Vacuum was applied for 1½ hours. The flask was purged with dry nitrogen three times before venting with nitrogen. The flask was then placed in a preheated (70° C.) oil bath; the temperature was then reset to 120° C. Approximately 15 minutes after the introduction of the reactor into the bath, the bath temperature reached 120° C. After maintaining a temperature of 120° C. for 13 minutes, the agitator was partially lowered into the reaction mass and was set to maintain a slow agitation speed. Two minutes later, the temperature was reset to 140° C., which was achieved in 5 minutes. When the 140° C. temperature was achieved, the stirrer was lowered slightly further. The 140° C. temperature was maintained for 5 minutes, and the temperature was then reset to 210° C. After 10 minutes, the stirrer was fully lowered into the milky reaction mass. It required a total of 15 minutes to reach 210° C. After reaching 210° C., the temperature was reset to 215° C., which was reached in 2 minutes. After 5 minutes at 215° C., the reaction mass started to clear and within another 8 minutes it was completely clear and becoming viscous. The temperature of 215° C. was maintained for 2 hours, after which the vessel was removed from the oil bath and allowed to cool.

The copolymer was isolated, ground, and dried in vacuo at room temperature and then at 110° C. (the time at 110° C. was 32 hours) to remove any unreacted monomer. A weight loss of 7.3% was observed. The resulting copolymer had a melting temperature (by hot stage microscopy) of 200° C. with some trace of the material melting at 211°–216° C. The copolymer exhibited a single phase melt and was recrystallizable. The polymer had an IV of 1.65 dl/g.

EXAMPLE 7

Preparation of Dyed Poly(p-dioxanone-co-glycolide) block copolymer at 50/50 initial weight composition A flame dried, 250 ml, round bottom, single neck flask was charged with 62.5 g of the dyed PDO. The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible.

The vessel was removed from the oil bath and allowed to cool. Sixty-two and one-half grams of pure glycolide monomer was introduced into the flask under dry nitrogen. The flask was then outfitted with a flame dried mechanical stirrer and an adapter with a hose connection. Vacuum was applied for 1½ hours. The flask was purged with dry nitrogen three times before venting with nitrogen. The flask was then placed in a preheated (70° C.) oil bath; the temperature was then reset to 120° C. Approximately 10 minutes after the introduction of the reactor into the bath, the bath temperature reached 120° C. After maintaining a temperature of 120° C. for 10 minutes, the agitator was partially lowered into the reaction mass and was set to maintain a very slow agitation speed. After an additional 5 minutes, the temperature was reset to 140° C. Five minutes later, complete melt was observed and the stirring rate was slightly increased. Five minutes thereafter, the temperature was reset to 210° C. and the agitator was fully lowered into the reaction mass. It required a total of 18 minutes to reach 210° C. After reaching 210° C., the temperature was reset to 215° C., which was reached in 2 minutes. The viscosity of the reaction mass increased quickly thereafter and the stirring rate was slowed significantly. The temperature of 215° C. was maintained for 1 hour, after which the vessel was removed from the oil bath and allowed to cool.

The copolymer was isolated, ground, and dried in vacuo at room temperature and then at 110° C. (the time at 110° C. was 32 hours) to remove water and any unreacted monomer. A weight loss of 6.7% was observed. The resulting copolymer had a melting temperature (by hot stage microscopy) of 202° C. with some trace of the material melting at 217° C. The copolymer exhibited a single phase melt and was recrystallizable. The polymer had an IV of 1.65 dl/g.

EXAMPLE 8

Preparation of Poly(p-dioxanone-co-glycolide) block copolymer at 60/40 initial weight composition A flame dried, 250 ml, round bottom, single neck flask was charged with 75.0 g of PDO. The flask was equipped with a vacuum adapter. Vacuum was applied and the flask was lowered into a silicone oil bath heated to 80° C.; heating at 80° C. under high vacuum was maintained for 16 hours to remove any residual water and to remove as much residual monomer as possible.

The vessel was removed from the oil bath and allowed to cool. Fifty grams of pure glycolide monomer was introduced into the flask under dry nitrogen. The flask was then outfitted with a flame dried mechanical stirrer and an adapter with a hose connection. Vacuum was applied for 1½ hours. The flask was purged with dry nitrogen three times before venting with nitrogen. The flask was then placed in a preheated (70° C.) oil bath; the temperature was then reset to 120° C. Approximately 12 minutes after the introduction of the reactor into the bath, the bath temperature reached 120° C. After maintaining a temperature of 120° C. for 15 minutes, the temperature was reset to 140° C. The agitator was partially lowered to begin stirring at a slow rate when 140° C. was reached in 6 minutes. After 5 minutes at 140° C., the temperature was reset to 205° C. and the stirrer was lowered further. Within 17 minutes, 205° C. was reached and the temperature was reset to 215° C. The final temperature was attained in an additional 3 minutes. The stirrer was fully lowered into the reaction mass. A temperature of 215° C. was maintained for a total of 2 hours, after which the vessel was removed from the oil bath and allowed to cool.

The copolymer was isolated, ground, and dried in vacuo at room temperature and then at 110° C. (time at 110° C. was 32 hours) to remove any unreacted monomer. A weight loss of 9.5% was observed. The resulting copolymer had a melting range (by hot stage microscopy) of 160°–180°, with some trace of the material melting at 187° C. The copolymer exhibited a single phase melt and was recrystallizable. The polymer had an IV of 1.53 dl/g.

EXTRUSION

In the preparation of fibers, especially surgical filaments, the copolymers are melt extruded through a spinnerette in a conventional manner to form one or more filaments, in accordance with the following general procedure used for laboratory scale experiments.

Extrusion of the copolymers described herein was accomplished using an INSTRON Capillary Rheometer or a single screw extruder. The copolymers evaluated in the INSTRON Capillary Rheometer were packed in the preheated (120° for Example 9, 150° C. for the remaining Examples) extrusion chamber and extruded through a 40 mil die ($L/D=24.1$) after a dwell time of 9 to 13 minutes at the extrusion temperature and a ram speed of 2 cm/min and a shear rate of 213 sec$^{-1}$. While extrusion temperatures depend both on the polymer Tm and on the melt viscosity of the material at a given temperature, extrusion of the subject copolymers at temperatures of about 10° to 75° C. above the Tm is usually satisfactory. The extrusion temperatures of the example copolymers described herein ranged from 200° to 230° C. The extrudate typically was taken up through an ice water quench bath at 24 feet/minute, although other bath temperatures and take-up speeds occasionally were used.

The extrudate filaments (which have been allowed to crystallize sufficiently—usually, storage of the extruded filament at room temperature for 1 to 24 hours will suffice to permit the requisite crystallization to take place—alternatively, the fibers may be annealed at elevated temperature prior to drawing. Some of the examples described herein were annealed at 60° C. for 30 to 45 minutes prior to drawing.) are subsequently drawn about 5× to 7.5× in a one or multistage drawing process in order to achieve molecular orientation and improve tensile properties. The manner of drawing is as follows:

The extrude (diameter range, usually 16–20 mils) passed through rollers at an input speed of four feet per minute and into a heated draw bath of glycerine. The temperatures of the draw bath can vary from about 25° to about 120° C.; the examples described herein employ temperatures between 52° and 55° C. The draw ratio in this first stage of drawing can vary from 3× to about 7×; the examples described herein employ draw ratios from 4× to 5×.

The partially drawn fibers are then placed over a second set of rollers into a glycerine bath (second stage) kept at temperatures ranging from 50° to about 120° C.; the examples described herein employ second stage draw temperatures of 72° to 75° C. Draw ratios of up to about 2× are applied in this second stage, but a ratio range of from 1.25× to 1.4× was employed in the examples. The fiber is passed through a water-wash, taken up on a spool, and dried. A set of hot rollers can be substituted for a portion or all of the glycerine draw bath. The resulting oriented filaments develop good straight and knot tensile strengths.

Dimensional stability of the oriented filaments may be enhanced by subjecting the filaments to an annealing treatment. This treatment consists of heating the drawn filaments to a temperature of from about 40° to about 130° C., most preferably from about 55° to 110° C. while restraining the filaments to prevent any substantial shrinkage. This process may begin with the filaments initially under tension or with up to 20% shrinkage allowed prior to restraint. The filaments are held at the annealing temperature for a few minutes to several days or longer depending on the temperature and processing conditions. In general, annealing for up to about 24 hours is satisfactory for the copolymers of the invention. Optimum annealing time and temperature for maximum fiber in vivo strength retention and dimensional stability is readily determined by simple experimentation for each fiber composition. The filaments thus produced may be fabricated into sutures or ligatures, attached to surgical needles, packaged, and sterilized by known techniques.

The characteristic properties of the filaments of the invention are readily determined by conventional test procedures. The tensile properties (i.e., straight and knot tensile strengths, Young's Modulus, and elongation) displayed herein were determined with an INSTRON tensile tester. The settings used to determine the straight tensile, knot tensile break elongation, and Young's Modulus were the following, unless indicated:

|  | Gauge Length (in) | Chart Speed (in/min) | Crosshead Speed (in/min) |
| --- | --- | --- | --- |
| Straight Tensile | 2 | 10 | 2 |
| Knot Tensile | 2 | 10 | 2 |
| Break Elongation | 2 | 10 | 2 |
| Young's Modulus | 2 | 10 | 2 |

The straight tensile strength is calculated by dividing the force to break by the initial cross-sectional area of the fiber. The elongation at break is read directly from the stress-strain curve. Young's Modulus is calculated from the slope of the stress-strain curve of the sample in the linear elastic region.

The knot tensile strength of a fiber is determined in separate experiments. The test article is tied into a surgeon's knot with one turn of the filament around flexible tubing of ¼ inch inside diameter and 1/16 inch wall thickness. The surgeon's knot is a square knot in which the free end is first passed twice, instead of once, through the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

The tensile strength values and Young's modulus (Y.M ) are reported as KPSI, or PSI$\times 10^3$.

Table I, below, displays the conditions used to produce extruded filaments from the copolymers of Examples 2-9.

TABLE I

Extrusion and Orientation Conditions

| | | | Orientation | | |
| | | | 1st Stage | | 2nd Stage |
| Ex. | Extrusion Temp, °C. | Extrudate Diam., mils | Draw Ratio | Temp °C. | Draw ratio | Temp °C. |
| --- | --- | --- | --- | --- | --- | --- |
| 2 | 230 | 18–19 | 5× | 55 | 1.4× | 72 |
| 3 | 230 | 17–18.5 | 5× | 53 | 1.4× | 72 |
| 4 | 225[2] | NA[3] | 4× | 53 | 1.25× | 75 |
| 5 | 215[1] | NA | 4× | 52 | 1.25× | 73 |
| 6 | 220[1] | 16.0–18.5 | 4× | 53 | 1.375× | 75 |
| 7 | 220[1] | 16.5–17.5 | 4× | 55 | 1.375× | 75 |
| 8 | 200[1] | 17.5–18.0 | 5× | 54 | 1.3× | 72 |

[1]Extrudate annealed @ 60° C. 30 minutes before drawing
[2]Extrudate annealed @ 60° C. 45 minutes before drawing
[3]NA means not available Representative physical properties of the monofilaments prepared as set forth above are displayed in Table II, below.

TABLE II

| | | Physical Properties | | | |
| Ex. | Anneal | Dia. mils | Straight kpsi | Knot kpsi | Elong. % | Mod. kpsi |
| --- | --- | --- | --- | --- | --- | --- |
| 2 | no | 6.7 | 54.7 | 54.7 | 74 | 664 |
| 2 | yes[1] | 6.7 | 47.2 | 36.8 | 40 | 627 |
| 3 | no | 6.1 | 67.4 | 41.1 | 48 | 591 |
| 3 | yes[2] | 6.3 | 57.7 | 52.6 | 53 | 551 |
| 4 | no | 7.8 | 109.7 | 78.7 | 49 | 356 |
| 4 | yes[2] | 7.7 | 115.1 | 81.8 | 45 | 591 |
| 5 | no | 7.7 | 88.0 | 71.7 | 71 | 47.2 |
| 5 | yes[2] | 7.5 | 98.5 | 74.0 | 56 | 230 |
| 5 | yes[1] | 8.4 | 88.6 | 59.5 | 60 | 137 |
| 6 | no | 7.9 | 96.1 | 67.9 | 77 | 75.4 |
| 7 | no | 8.0 | 97.5 | 70.6 | 87 | 83.6 |
| 8 | no | 6.0 | 157.4 | 92.0 | 94 | 80.9 |
| 8 | yes[3] | 7.5 | 104.1 | 54.6 | 67 | 92.6 |

[1]12 hours at 78° C.
[2]12 hours at 58° C.
[3]6.5 hours at 80° C.

What is claimed is:

1. A glycolide/p-dioxanone block copolymer which consists essentially of from 40 to 90 weight percent polymerized glycolide, the remainder being polymerized p-dioxanone, and which has an overall crystallinity of from about 25 to 45 percent, a glycolide-based crystallinity of from about 15 to 40 percent, and a melting temperature, by hot stage microscopy, within the range of from 140° C. to about 230° C.

2. The glycolide/p-dioxanone block copolymer of claim 1 wherein said copolymer contains greater than 50 weight percent polymerized glycolide.

3. The glycolide/p-dioxanone block copolymer of claim 1 wherein said copolymer contains greater than 60 weight percent polymerized glycolide.

4. A dimensionally stable, drawn, and oriented surgical filament comprising the block copolymer of claim 1, said filament having a straight tensile strength greater than about 30,000 psi and Young's modulus below about 700,000 psi, and wherein said filament loses from 50 to 100 percent of its strength within two weeks after implantation in the body.

5. A dimensionally stable, drawn, and oriented surgical filament comprising the block copolymer of claim 2, said filament having a straight tensile strength greater than about 30,000 psi and Young's modulus below about 700,000 psi, and wherein said filament loses from 50 to 100 percent of its strength within two weeks after implantation in the body.

6. A dimensionally stable, drawn, and oriented surgical filament comprising the block copolymer of claim 3, said
    tensile strength greater than 30,000 psi and Young's modulus below about 700,000 psi, and wherein said filament loses from 50 to 100 percent of its strength within two weeks after implantation in the body.

7. The filament of claim 4 in the form of a monofilament.

8. The filament of claim 4 in the form of a braid.

9. The filament of claim 4 in the form of a sterile suture.

10. The sterile suture of claim 9 attached to a surgical needle.

* * * * *

UNITED STATES PATENT AND TRADEMARK OFFICE
CERTIFICATE OF CORRECTION

PATENT NO. : 4,838,267

DATED : June 13, 1989

INVENTOR(S) : Dennis D. Jamiolkowski et al.

It is certified that error appears in the above-identified patent and that said Letters Patent is hereby corrected as shown below:

Claim 6, column 12, lines 46-50, after the word "said" should read

-- filament having a straight tensile strength greater than about 30,000 psi and Young's modulus below about 700,000 psi, and wherein said filament loses from 50 to 100 percent of its strength within two weeks after implantation in the body. --.

Signed and Sealed this

Thirteenth Day of March, 1990

Attest:

JEFFREY M. SAMUELS

*Attesting Officer*  *Acting Commissioner of Patents and Trademarks*